(12) United States Patent
Barnes

(10) Patent No.: US 11,109,894 B2
(45) Date of Patent: Sep. 7, 2021

(54) APPARATUS, SYSTEM, AND METHOD FOR SPINAL VERTEBRAE STABILIZATION

(71) Applicant: DR. BRYAN BARNES PC, Athens, GA (US)

(72) Inventor: Bryan Barnes, Athens, GA (US)

(73) Assignee: DR. BRYAN BARNES PC, Athens, GA (US)

( * ) Notice: Subject to any disclaimer, the term of this patent is extended or adjusted under 35 U.S.C. 154(b) by 48 days.

(21) Appl. No.: 16/336,317

(22) PCT Filed: Sep. 26, 2017

(86) PCT No.: PCT/US2017/053426
§ 371 (c)(1),
(2) Date: Mar. 25, 2019

(87) PCT Pub. No.: WO2018/058102
PCT Pub. Date: Mar. 29, 2018

(65) Prior Publication Data
US 2020/0022734 A1 Jan. 23, 2020

Related U.S. Application Data

(60) Provisional application No. 62/399,672, filed on Sep. 26, 2016.

(51) Int. Cl.
*A61B 17/70* (2006.01)
(52) U.S. Cl.
CPC ...... *A61B 17/7035* (2013.01); *A61B 17/7034* (2013.01); *A61B 17/7082* (2013.01)

(58) Field of Classification Search
CPC ............ A61B 17/7086; A61B 17/7079; A61B 17/7077; A61B 17/708; A61B 17/7088; A61B 17/7089; A61B 17/7085
See application file for complete search history.

(56) References Cited

U.S. PATENT DOCUMENTS

| 5,720,751 | A | 2/1998 | Jackson |
| 7,722,617 | B2 * | 5/2010 | Young ................ A61B 17/7086 606/86 A |
| 7,846,093 | B2 | 12/2010 | Gorek et al. |
| 8,216,282 | B2 | 7/2012 | Hua |
| 8,545,541 | B2 | 10/2013 | Hua |

(Continued)

OTHER PUBLICATIONS

International Preliminary Report on Patentability issued for Application No. PCT/US2017/053426, dated Apr. 4, 2019, 11 pages.

(Continued)

*Primary Examiner* — Jan Christopher L Merene
(74) *Attorney, Agent, or Firm* — Meunier Carlin & Curfman LLC

(57) ABSTRACT

Provided are improved pedicle screws or lateral mass screws, systems and methods for stabilizing spinal vertebrae, such as a pedicle or lateral vertebral mass, during minimally invasive spinal surgery. For example, provided is a pedicle screw or lateral mass screw having a screw shaft comprising an elongated threaded body having a vertical axis, a polyaxial screw head comprising two opposite walls that define a concave channel, and two semi-rigid, non-wire, elongated projections extending from two opposite walls of the polyaxial screw head at a positive angle in relation to a horizontal plane.

6 Claims, 9 Drawing Sheets

(56) References Cited

U.S. PATENT DOCUMENTS

| | | |
|---|---|---|
| 8,556,940 B2 | 10/2013 | Hua |
| 9,198,692 B1 | 12/2015 | Doose et al. |
| 2007/0073294 A1 | 3/2007 | Chin |
| 2007/0106123 A1 | 5/2007 | Gorek et al. |
| 2007/0233079 A1 | 10/2007 | Fallin et al. |
| 2008/0015601 A1* | 1/2008 | Castro .............. A61B 17/7091 606/86 R |
| 2008/0161857 A1 | 7/2008 | Hestad et al. |
| 2009/0221878 A1 | 9/2009 | Gorek |
| 2009/0222044 A1 | 9/2009 | Gorek |
| 2009/0222046 A1 | 9/2009 | Gorek |
| 2009/0228051 A1* | 9/2009 | Kolb ................ A61B 17/7032 606/305 |
| 2011/0087293 A1 | 4/2011 | Ferreira et al. |
| 2011/0172714 A1 | 7/2011 | Boachie-Adjei et al. |
| 2011/0301647 A1 | 12/2011 | Hua |
| 2012/0022597 A1 | 1/2012 | Gephart |
| 2012/0253413 A1 | 10/2012 | Runco |
| 2016/0038195 A1 | 2/2016 | Genovese et al. |
| 2016/0106480 A1 | 4/2016 | Zhou et al. |
| 2017/0164980 A1* | 6/2017 | Le Roux .............. A61B 17/708 |

OTHER PUBLICATIONS

Supplementary European Search Report issued in corresponding application No. EP 17854120, dated Apr. 30, 2020; 10 pages.
PCT/US17/53426; International Search Report and Written Opinion dated Nov. 27, 2017, 12 pages.

* cited by examiner

APPARATUS, SYSTEM, AND METHOD FOR SPINAL VERTEBRAE STABILIZATION

CROSS-REFERENCE TO RELATED APPLICATIONS

This application is a national stage application filed under 35 U.S.C. § 371 of PCT/US2017/53426 filed Sep. 26, 2017, which claims the benefit of U.S. Provisional Patent Application No. 62/399,672 filed Sep. 26, 2016, the content of which is incorporated herein by reference in its entirety.

TECHNICAL FIELD

This disclosure relates to minimally invasive spinal surgery, and more particularly, to pedicle screws or lateral mass screws for spinal vertebrae stabilization.

BACKGROUND

The spine includes a plurality of vertebrae arranged in a vertical column. Traditionally, implant devices have been secured to bone or bone segments to promote the healing and repair of various parts of the human body. There is an intervertebral disc between each vertebrae that provides a cushion between adjacent vertebrae and transmits force between adjacent vertebrae. Traditionally, degenerative disc disease has been treated by surgically removing a diseased disc and inserting an implant in the space vacated by the diseased disc. The implant may be a bone or other biocompatible implant. The adjacent vertebrae are then immobilized relative to one another using pedicle screw or lateral mass screw fixation. Subsequently, the adjacent vertebrae grow into one solid piece of bone over time. This process can include using a bone graft or bone graft substitute to stabilize the vertebrae.

Conventionally, spinal rods that immobilize vertebral bones are typically anchored to the vertebrae through bone screws that extend through the pedicle or lateral mass into vertebral bodies or bones by hooks that engage around the vertebrae. Spinal rods have been used that are connected to each screws or anchor. While incisions are required during many surgical procedures to gain access to the site, such incisions can cause injury to the patients' body. To avoid unnecessary damage, small incisions are often preferred.

Many traditional approaches of spinal vertebrae stabilization require the use of flexible guidewires to designate where a pedicle screw or lateral mass screw is to be implanted and then use some minimally invasive surgical (MIS) system during surgery to anchor the screw to the mass. In one traditional approach, the MIS system uses at least two pedicle anchors or screws, in which the screws are secured to the vertebrae by sliding the MIS device down a guidewire, like the MIS implant device described in U.S. Patent App. No. 2012/0022597. As described therein, the procedure includes a surgeon inserting a Jamshidi needle percutaneously over the posterior spinal anatomy thereby creating a small incision. The Jamshidi needle is able to hold the guidewire and is used to percutaneously force the guidewire into place. It is only after the guidewire is secured that a docking device is used to secure an anchor to a vertebral mass. Traditionally this is done by sliding the docking device down the guidewire towards the pre-positioned guidewire path.

Additionally, prior art systems for performing transforaminal lumbar interbody fusion and other interbody fusions in the spine have been known to use a monoaxial pedicle screw having detachably connected flexible guidewires for guiding a rod down to the screw, like the system disclosed in U.S. Pat. No. 8,556,940. As provided therein, the system relies on attaching non-circular rigid shafts or circular flexible wires to a pedicle screw head, directly guiding a rod down to a screw using the flexible guidewires or rigid shafts, and directly guiding a locking assembly down to the screw head.

However, the use of the flexible wires in spinal stabilization surgeries has been prone to several issues, including for example, entanglement of the wires and the high cost of having to purchase separate guidewires for attachment to pedicle screws. The use of rigid non-circular shafts for guiding tools is similarly problematic, as rigid shafts cannot accommodate to the dimensions of various docking tools since the shafts cannot be readily flexed by doctors in real-time during surgical procedures.

SUMMARY

Provided are improved pedicle screws or lateral mass screws, systems and methods for stabilizing a spinal vertebra, such as a pedicle or lateral vertebral mass, during minimally invasive spinal surgery.

In an example embodiment, the system includes a pedicle screw or lateral mass screw having a screw shaft comprising an elongated threaded body having a vertical axis. The pedicle screw or lateral mass screw further includes a polyaxial screw head comprising two opposite walls that define a concave channel where each of the two opposite sidewalls include a respective top surface that defines a horizontal plane, the horizontal plane being perpendicular to the vertical axis. The pedicle screw or lateral mass screw further includes at least two semi-rigid, non-wire, elongated projections extending from the two opposite walls at a positive angle in relation to the horizontal plane where at least a portion of each of the two semi-rigid, non-wire, elongated projections is above the horizontal plane. Moreover, the two semi-rigid, non-wire, elongated projections are configured to have a height that is at or above a level of a skin incision after implantation of the pedicle screw or lateral mass screw in a spinal vertebrae, such as vertebral lateral mass, or a lumbar, thoracic, or cervical pedicle.

In certain example embodiments, the system and/or apparatus further includes at least one or more of the following devices: a hand-held fixation tool, a set screw, and a spinal fixation element such as a spinal stabilization rod.

The details of one or more embodiments of the disclosure are set forth in the accompanying drawings and the description below. Other features, objects, and advantages of the disclosure will be apparent from the description, drawings, and from the claims.

DESCRIPTION OF DRAWINGS

To facilitate an understanding of, and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Figure 1:
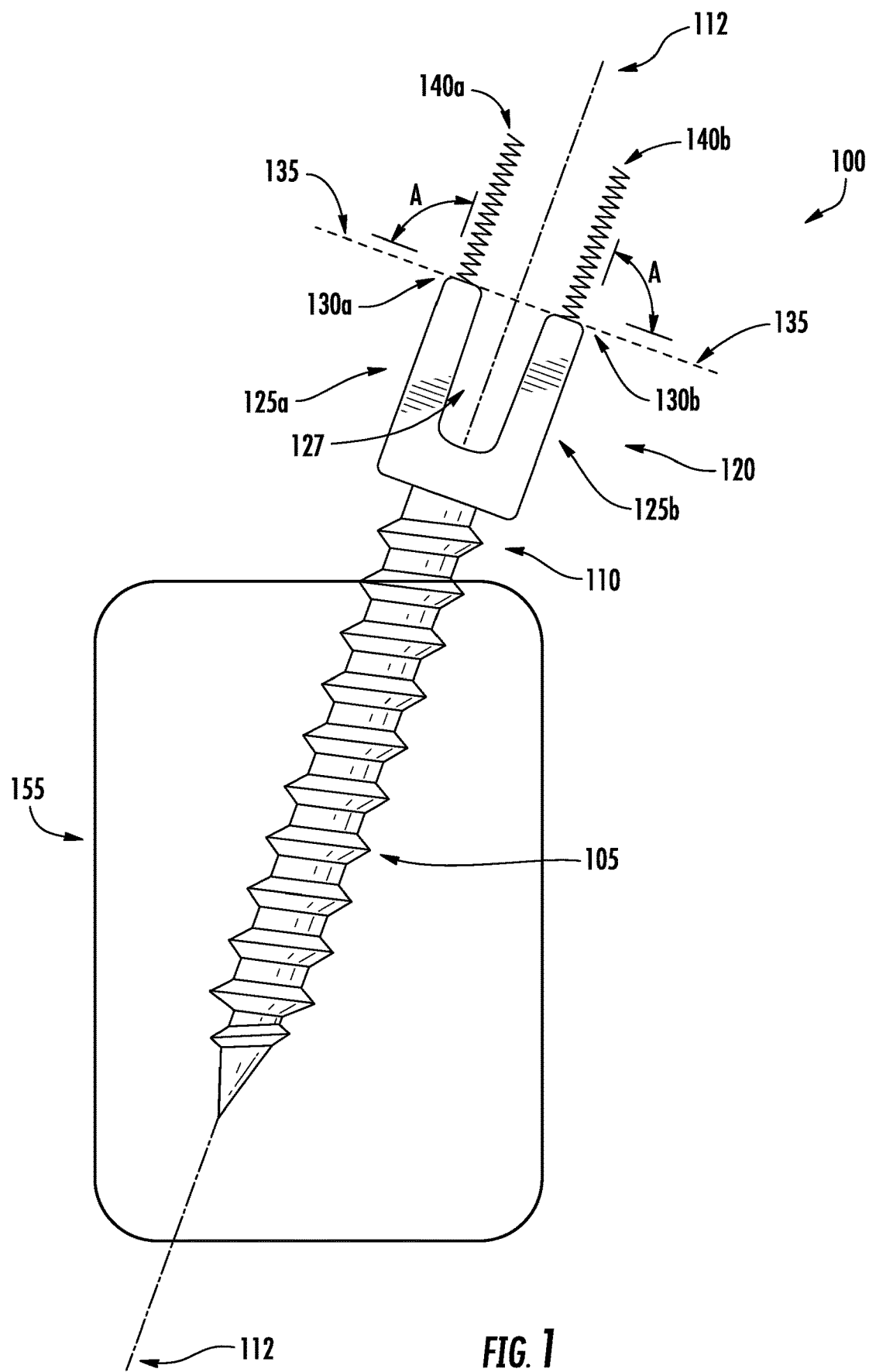
FIG. 1 is a perspective view of a MIS system that includes a pedicle screw or lateral mass screw fixed to a pedicle or lateral vertebral mass in accordance with the present disclosure.

The following is a description of several illustrations of improved minimally invasive surgical systems for treating spinal injuries and abnormalities.

Certain terminology is used herein for convenience only and is not to be taken as a limitation on the present invention. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," and "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

FIGS. 1-10 illustrate an example of minimally invasive surgical (MIS) system comprising one or more pedicle screws or lateral mass screws 100 in accordance with the present disclosure. In particular, the pedicle screw or lateral mass screw 100 can be configured to facilitate docking of a hand-held fixation tool 200 that locks a spinal fixation element 300, like a spinal stabilization rod, to the pedicle screw or lateral mass screw 100 for non-wire guided pedicle or lateral mass stabilization in accordance with the present disclosure, as will be discussed in further detail below (see FIGS. 3-7). The locking can be performed, for example, through the application of a set screw 400 to the polyaxial screw head 120, which will also be described in further detail below (see FIGS. 2, 4-5, 7, and 10).

As shown in FIG. 1, an example pedicle screw or lateral mass screw 100 includes a screw shaft 105, a polyaxial screw head 120, and two or more semi-rigid, non-wire, elongated projections 140a, 140b extending from the polyaxial screw head 120. In operation, the screw shaft 105 can be used to secure the pedicle screw or lateral mass screw 100 to a vertebral lateral mass or a lumbar, thoracic, or cervical pedicle 155 as shown in FIGS. 1 and 3-9. In certain embodiments, the screw shaft 105 of the pedicle screw or lateral mass screw 100 includes an elongated threaded body 110 having a vertical axis 112.

Although FIGS. 1-10 show the screw shaft 105 as being vertically aligned with the polyaxial screw head 120, it should be understood the screw shaft 105 may pivot or rotate in relation to the polyaxial screw head 120. In certain embodiments the screw shaft 105 is connected to the polyaxial screw head 120 via a polyaxial ball-and-socket joint at the base of the polyaxial screw head 120. In certain embodiments, the length of the pedicle screw or lateral mass screw shaft 105 is between about 10 millimeters and about 60 millimeters.

Figure 2:
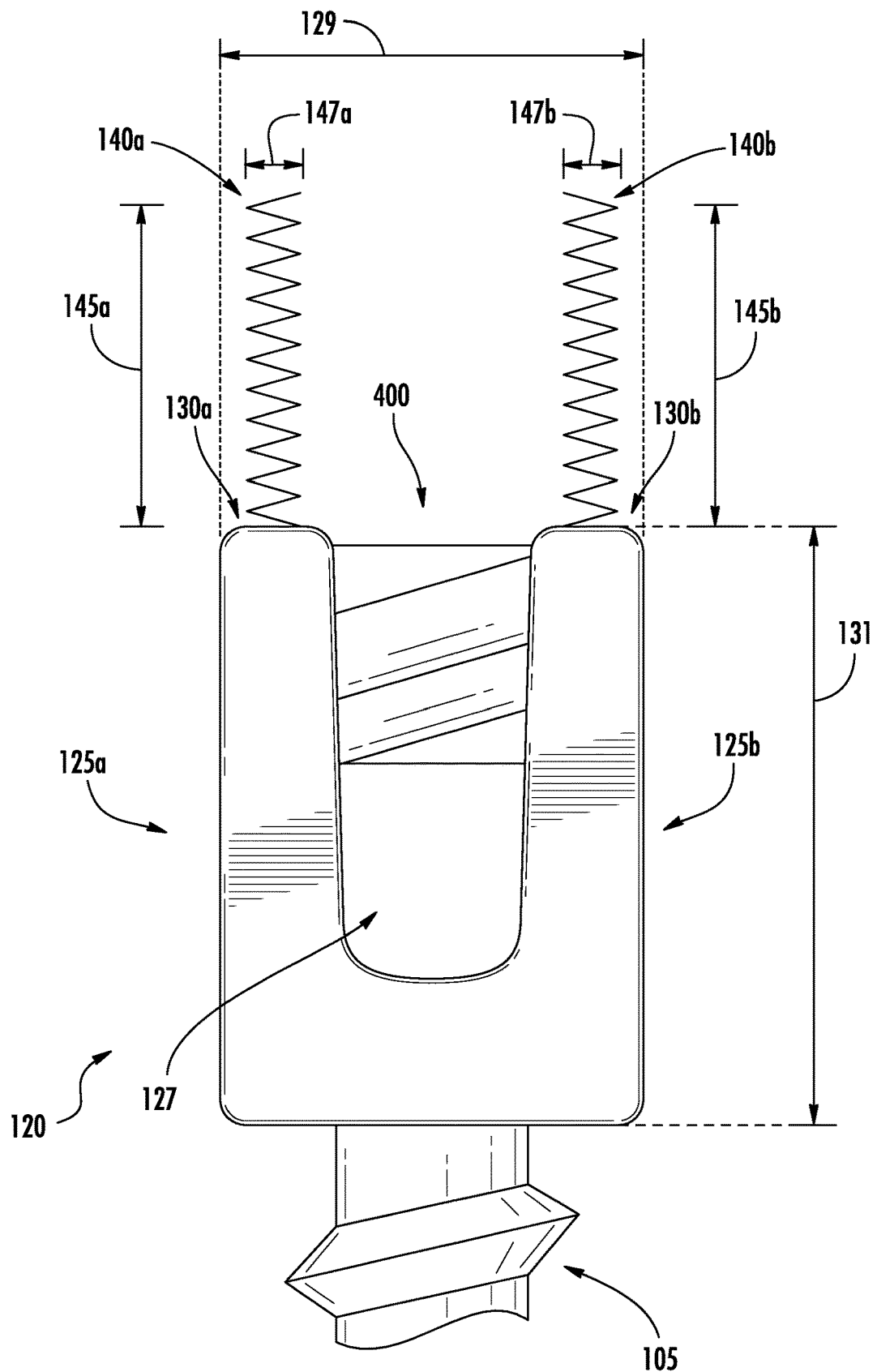
FIG. 2 is an exploded lateral side view of a MIS system that includes a pedicle screw or lateral mass screw and a set screw in accordance with the present disclosure.
Figure 3:
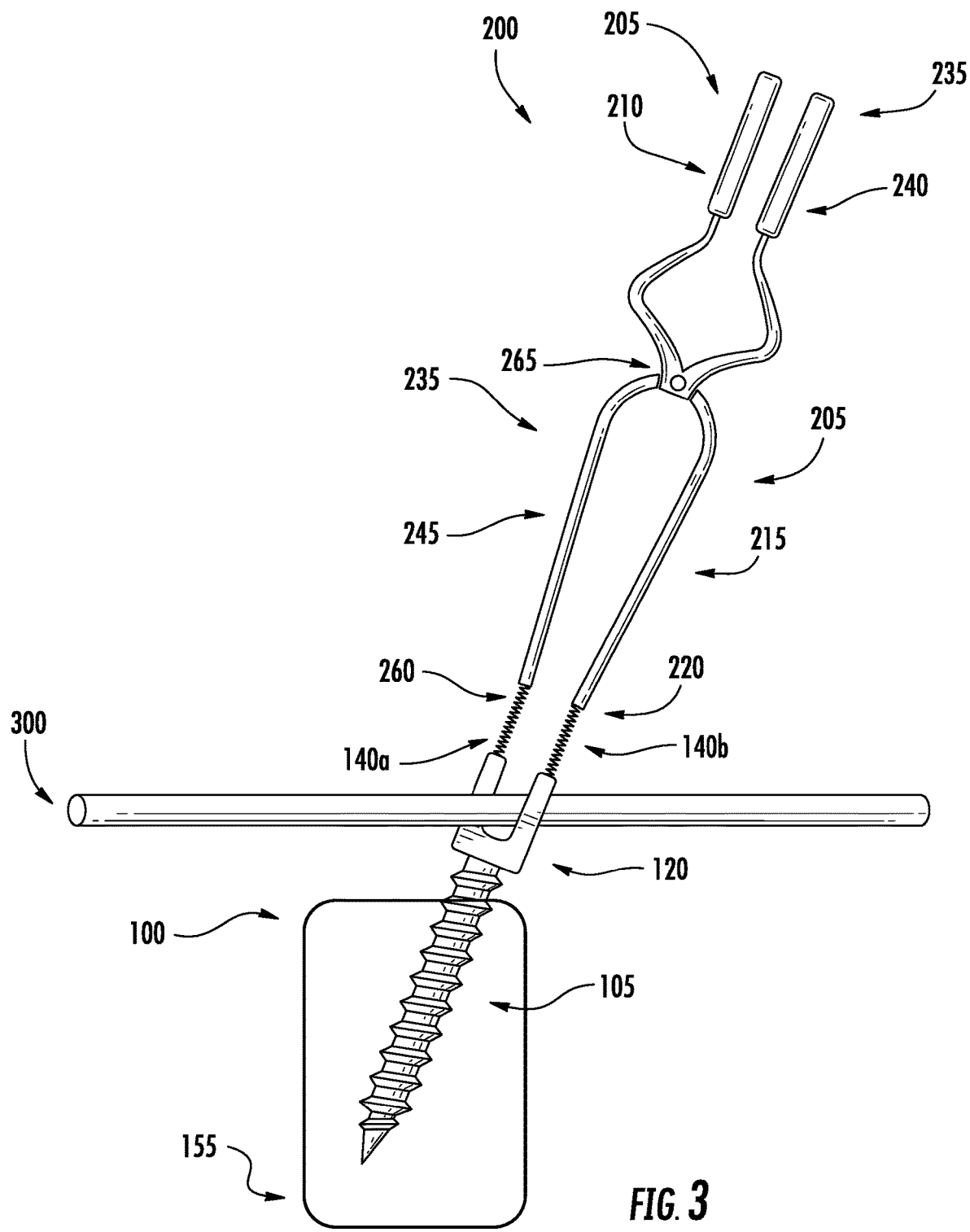
FIG. 3 is a perspective view of a MIS system that includes a pedicle screw or lateral mass screw fixed to a pedicle or lateral vertebral mass, a hand-held fixation tool, and a spinal fixation element in accordance with the present disclosure, the view showing the semi-rigid, non-wire, elongated projections of the pedicle screw or lateral mass screw being inserted into the hand-held fixation tool.
Figure 4:
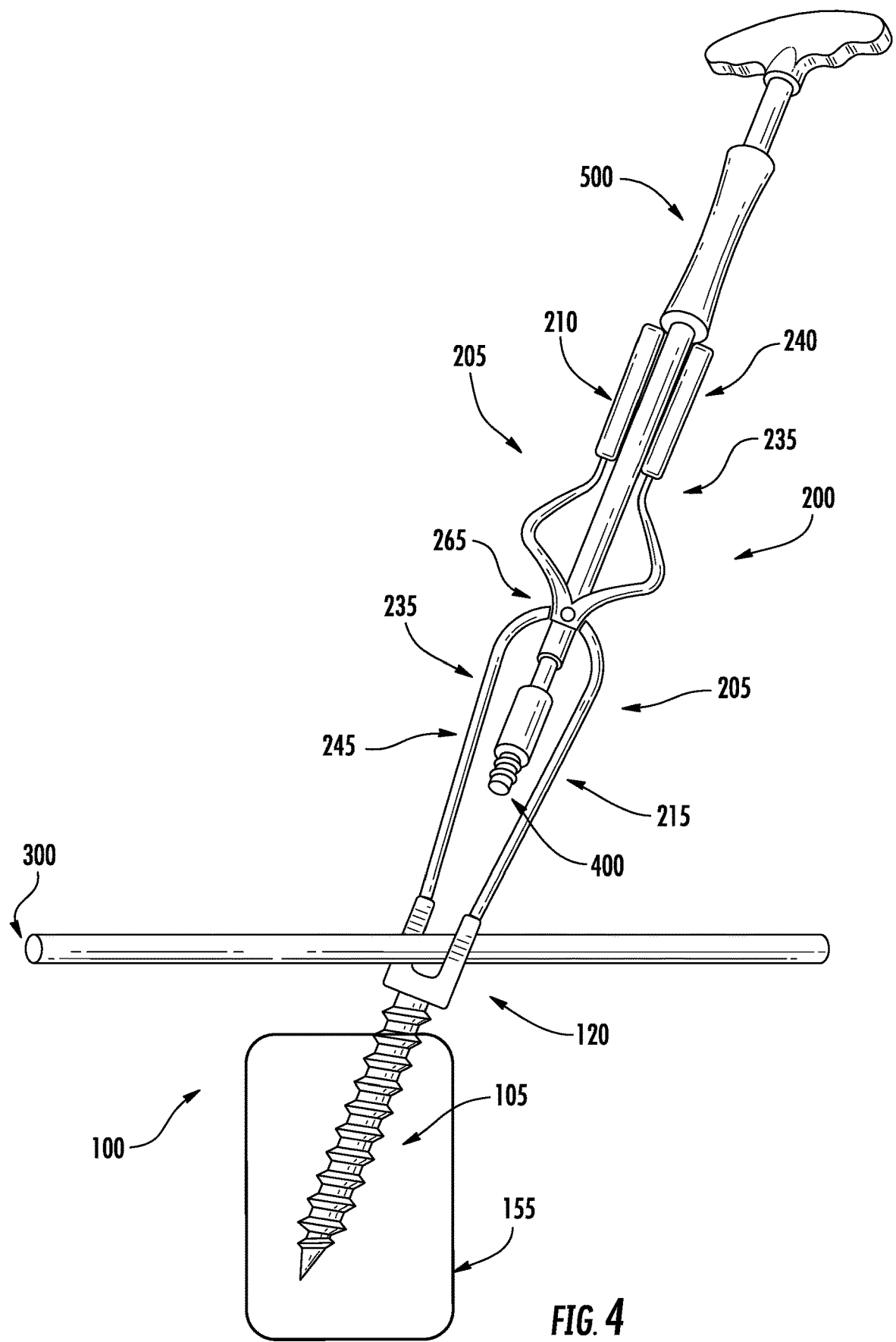
FIG. 4 is a perspective view of a MIS system that includes a pedicle screw or lateral mass screw fixed to a pedicle or lateral vertebral mass, a hand-held fixation tool including a screw driver, a spinal fixation element, and a set screw in accordance with the present disclosure, the view showing the hand-held fixation tool abutting the pedicle screw or lateral mass screw prior to inserting the set screw.
Figure 5:
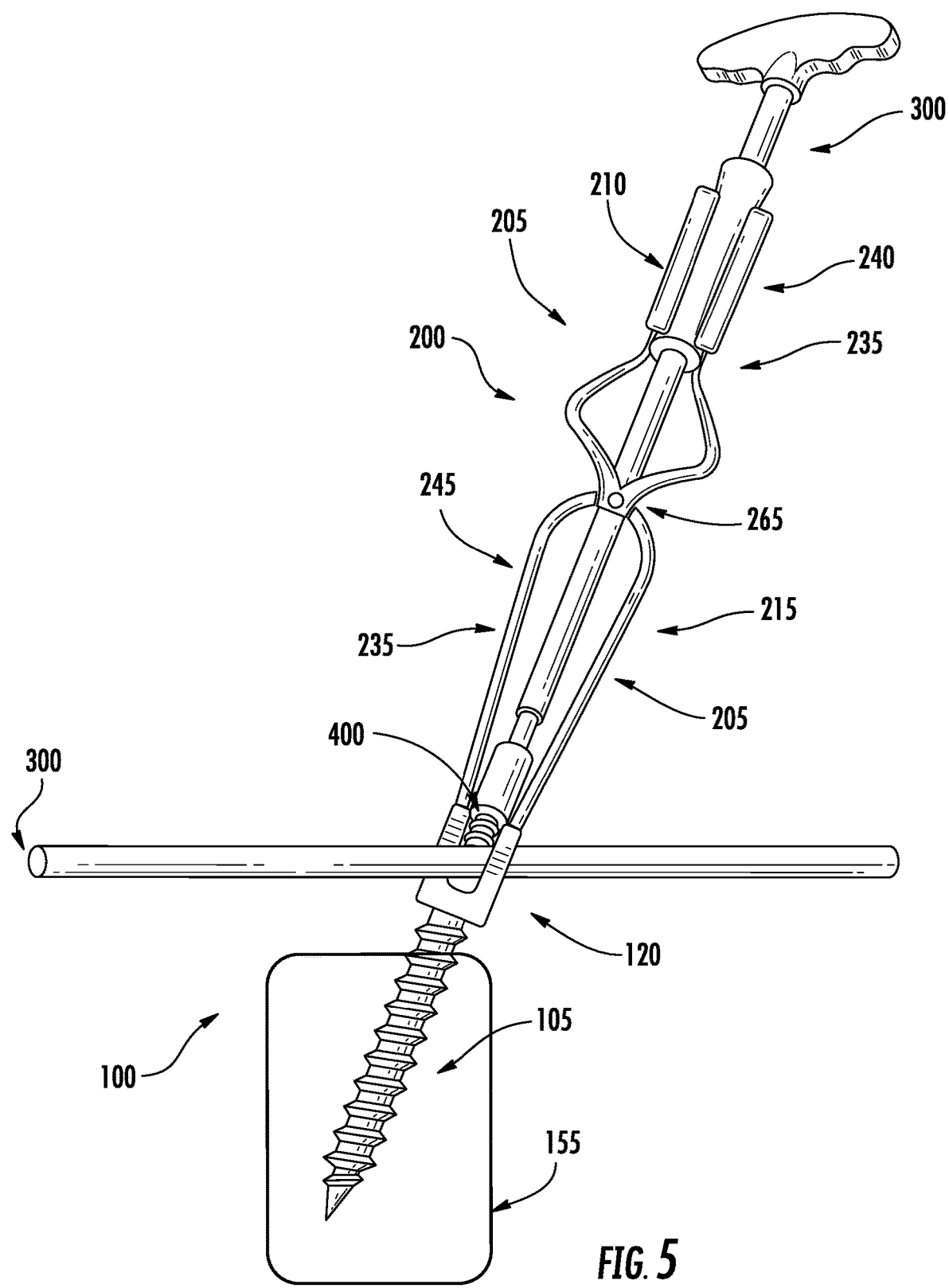
FIG. 5 is another perspective view of the MIS system of FIG. 4, the view showing the screw driver inserting the set screw to the polyaxial screw head of the pedicle screw or lateral mass screw above the spinal fixation element in accordance with the present disclosure.

As shown in FIGS. 1-10, in certain embodiments, the polyaxial screw head 120 of the pedicle screw or lateral mass screw 100 includes a U-shaped or tulip shaped head, which assists with retention of a spinal fixation element 300 (see FIGS. 3-9 for spinal fixation element 300). As shown in FIG. 2, the polyaxial screw head 120 of the example pedicle screw or lateral mass screw 100, includes two opposite walls 125a, 125b that define a concave channel 127. The channel 127 can be used to receive a spinal fixation element 300, like the spinal stabilization rod seen in FIGS. 3-9. The two opposite walls 125a, 125b of the polyaxial screw head 120 each include a respective top surface 130a, 130b that together define a horizontal plane 135 that is perpendicular to the vertical axis 112. In certain embodiments, the top surfaces 130a, 130b are substantially flat. In certain embodiments, the top surfaces 130a, 130b are contoured. In certain embodiments, the two opposite sidewalls 125a, 125b include a threaded inner surface (not shown) that can be used to receive a set screw 400 therebetween (see FIGS. 2, 4-5, 7 and 10 for set screw 400).

Referring back to FIG. 2, in certain embodiments the polyaxial screw head 120 has a width 129 that is between about 7 millimeters and about 16 millimeters, a height 131 that is between about 2 millimeters and about 25 millimeters, and a depth (not shown) that is between about 1 and about 5 millimeters. Other suitable screw head configurations, shapes, and sizes may be used.

As shown in FIG. 1, the two semi-rigid, non-wire, elongated projections 140a and 140b of the example screw 100 extend from the two opposite walls 125a, 125b of the polyaxial screw head 120 at a positive angle A in relation to the horizontal plane 135. In certain embodiments, the positive angle A is selected from a range of angles that include for example, about 5 degrees to (and including) about 90 degrees. In certain embodiments the angle is one of the following: about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees. During surgical operations, the positive angle A may fluctuate within the range of angles listed above when force is applied by a doctor to the semi-rigid, non-wire, elongated projections 140a and 140b. When external force is absent or removed, the non-wire, elongated projections 140a and 140b are able to maintain or revert to the selected positive angle A.

In certain embodiments, each of the two semi-rigid, non-wire, elongated projections 140a, 140b include a portion 150a, 150b that resides above the horizontal plane 135. In certain embodiments, the two semi-rigid, non-wire, elongated projections 140a, 140b are removable via mechanical separation. Mechanical separation can include, for example, cutting.

As shown in FIG. 2, in certain embodiments, the two semi-rigid, non-wire, elongated projections 140a, 140b each have a height 145a, 145b that is at or above a level of a skin incision after implantation of the pedicle screw or lateral mass screw 100 into a vertebral lateral mass or a lumbar, thoracic, or cervical pedicle 155. This height would assist in the easy placement of the hand-held fixation tool 200, which is described in further detail below (see FIGS. 3-7). In certain embodiments, the height 145a, 145b is between 3 centimeters and 10 centimeters.

As further shown in FIG. 2, in certain embodiments each of the semi-rigid, non-wire, elongated projections 140a, 140b includes a diameter 147a, 147b that is greater than 1 millimeter. In certain embodiments, each of the semi-rigid, non-wire, elongated projections 140a, 140b includes a helical body having a circular cross section. In certain embodiments, each of semi-rigid, non-wire, elongated projections 140a, 140b includes a cylindrical body (not shown).

As explained in the Background section above, prior art systems relied on attaching non-circular rigid shafts or circular flexible wires to pedicle screw heads to guide rods down to a screws and to guide locking assemblies down to screw heads. These types of flexible wires are often formed from nitinol, which is a nickel and titanium alloy having a low elastic modulus of about 48 gigapascals, or in some cases between 40-75 gigapascals. Traditionally, such flexible wires have a diameter that ranges from about 0.46 millimeters to about 1 millimeter. Examples of such wires include threads, strings, cords, and cables, and combinations therein such as bundles of threads, strings, cords, and cables.

In contrast to the prior art, the pedicle screw or lateral mass screw 100 disclosed herein utilizes semi-rigid, non-wire, elongated projections 140a, 140b that are made from a semi-rigid material having a elastic modulus that is higher than traditional flexible guidewires but lower than traditional rigid shafts and towers. The semi-rigid, non-wire, elongated projections 140a, 140b can be made from, for example, stainless steel, titanium, and, steel alloy or other suitable materials. In certain embodiments, the semi-rigid material used to create semi-rigid, non-wire, elongated projections 140a, 140b has an elastic modulus higher than about 40 gigapascals. In certain embodiments, the semi-rigid material used to create semi-rigid, non-wire, elongated projections 140a, 140b has an elastic modulus of about 200 gigapascals. As indicated above, the diameters 147a, 147b of the semi-rigid, non-wire, elongated projections 140a, 140b include a diameter that is greater than 1 millimeter and are thus thicker than conventional flexible guide wires. Other suitable materials or combinations of materials can be used to create the semi-rigid, non-wire, elongated projections 140a, 140b such that the semi-rigid, non-wire, elongated projections 140a, 140b do not excessively tangle or bend below the horizontal plane 135 during surgery.

In certain embodiments, the semi-rigid, non-wire, elongated projections 140a, 140b are pre-manufactured components of the polyaxial screw head 120. Thus, in certain embodiments, the semi-rigid, non-wire, elongated projections 140a, 140b are not attachments or add-on instruments to the pedicle screw or lateral mass screw 100, but rather are integrally formed features of the pedicle screw or lateral mass screw 100 itself.

In embodiments where the semi-rigid, non-wire, elongated projections 140a, 140b are a pre-manufactured part of the pedicle screw or lateral mass screw 100 itself, the semi-rigid, non-wire, elongated projections 140a, 140b provide an improvement over the prior art systems as the prior art systems generally required the use of screw extenders, towers, or blade retractors, which are add-on components for conventional screws. By pre-manufacturing the semi-rigid, non-wire, elongated projections 140a, 140b as part of the pedicle screw or lateral mass screw 100, the pedicle screw or lateral mass screw 100 disclosed herein may reduce the complexity of use for end-users, as well as potentially provide a reduction in cost by eliminating the need to purchase guidewires, towers, or other forms of add-on systems. Moreover, such a pre-manufactured design from a technical perspective is further unique as it does not require soldering or attaching of the semi-rigid, non-wire, elongated projections 140a, 140b to the pedicle screw or lateral mass screw 100 after manufacturing.

Referring back to FIGS. 3-7, in certain embodiments the MIS system further includes a hand-held fixation tool 200 configured to operatively engage the semi-rigid, non-wire elongated projections 140a, 140b. In one example, the hand-held fixation tool 200 includes a first scissor arm 205 having a first manual gripping end 210 and a first distal receiving shaft 215. The first distal receiving shaft 215 includes a first bore 220. The hand-held fixation tool 200 further includes a second scissor arm 235 having a second manual gripping end 240 and a second distal receiving shaft 245. The second distal receiving shaft 245 includes a second bore 260. The first and second scissor arms 205, 235 can be pivotably coupled about pivot axis 265, or other suitable locations for example. In certain embodiments, a first of the two semi-rigid, non-wire, elongated projections 140a is sized to fit within the first distal receiving shaft 215, and a second of the two semi-rigid non-wire, elongated projections 140b is sized to fit within the second distal receiving shaft 245. In certain embodiments, the diameters of the first and second bores 220, 235 are each greater than 1 millimeter.

In certain embodiments, the MIS system includes a spinal fixation element 300 that is configured to be retained in the polyaxial screw head 120 of the pedicle screw or lateral mass screw 100. In certain embodiments the spinal fixation element 300 is a spinal stabilization rod. In certain embodiments, the spinal fixation element 300 has a diameter that is between about 2.5 millimeters and about 10.5 millimeters.

Figure 6:
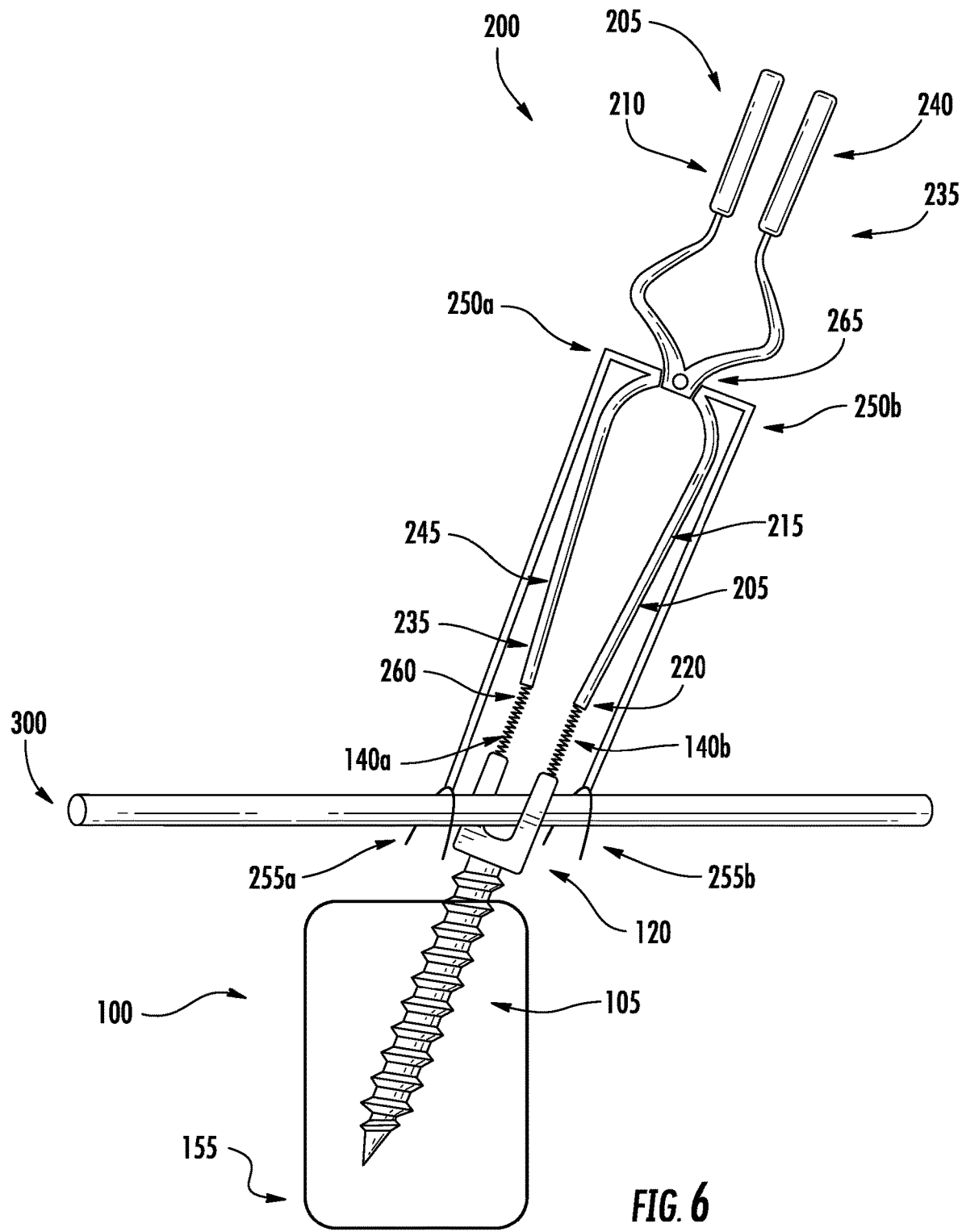
FIG. 6 is a perspective view of a MIS system that includes a pedicle screw or lateral mass screw fixed to a pedicle or lateral vertebral mass, a spinal fixation element, and a hand-held fixation tool having a pair of side arms having hook ends in accordance with the present disclosure, the view showing the semi-rigid, non-wire, elongated projections of the pedicle screw or lateral mass screw being inserted into the hand-held fixation tool and the hook ends of the side arms engaging the spinal fixation element.
Figure 7:
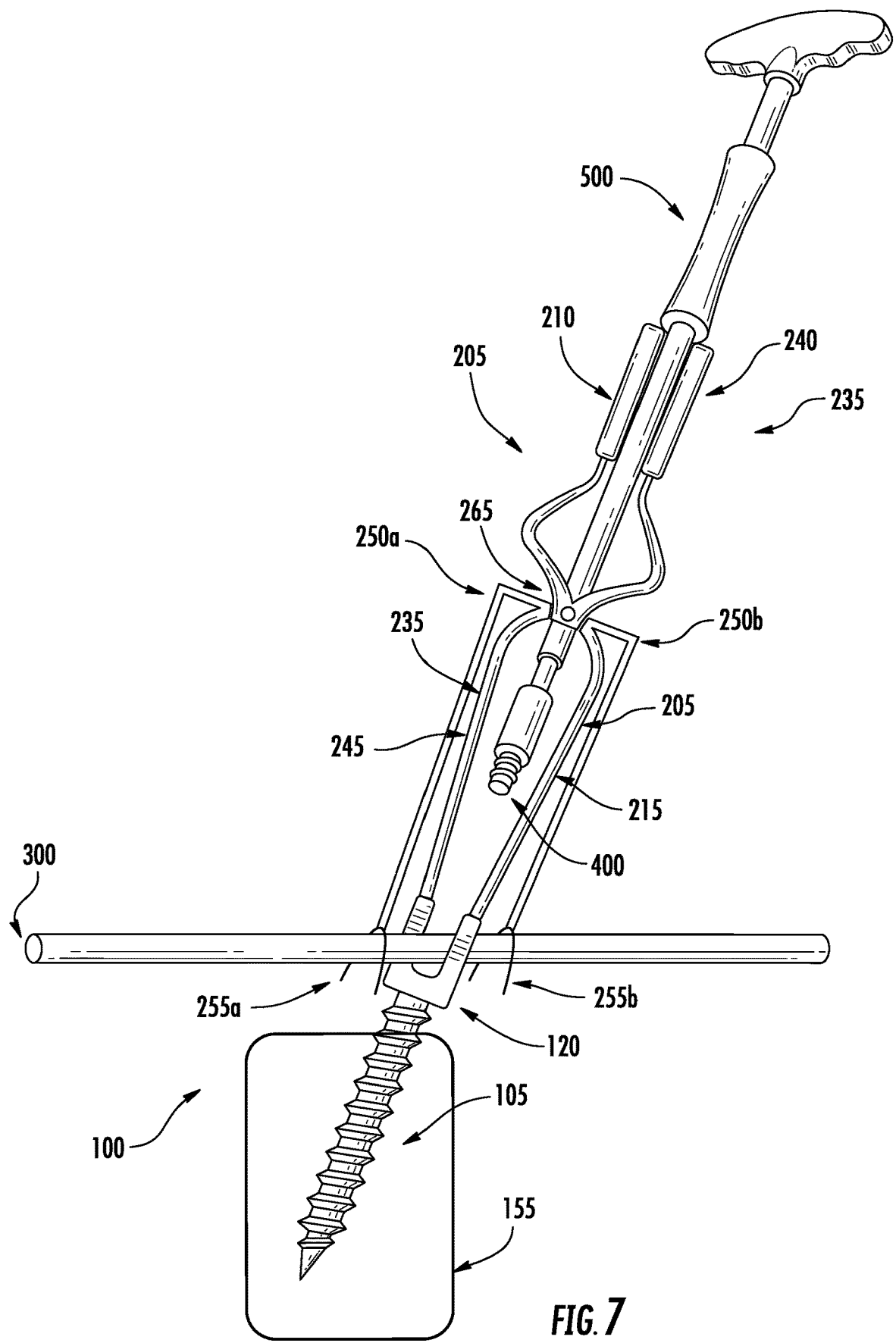
FIG. 7 is a perspective view of a MIS system that includes a pedicle screw or lateral mass screw fixed to a pedicle or lateral vertebral mass, a spinal fixation element, a set screw, and a hand-held fixation tool including a screw driver and a pair of side arms having hook ends in accordance with the present disclosure, the view showing the hand-held fixation tool abutting the pedicle screw or lateral mass screw prior to inserting the set screw.
Figure 8:
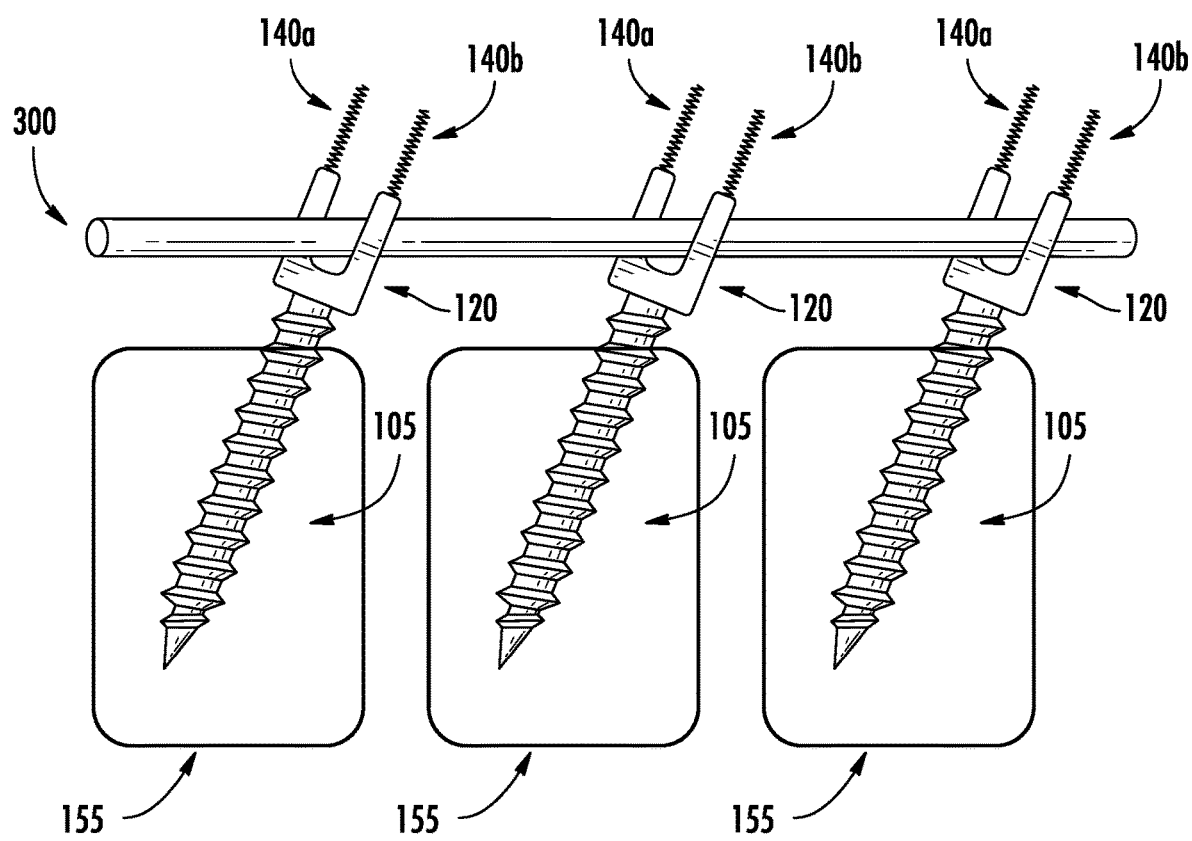
FIG. 8 is a perspective view of a MIS system that includes a plurality of pedicle screws or lateral mass screws fixed to a plurality of pedicles or lateral vertebral masses and a spinal fixation element situated in the polyaxial screw heads of the plurality of pedicle screws or lateral mass screws in accordance with the present disclosure.
Figure 9:
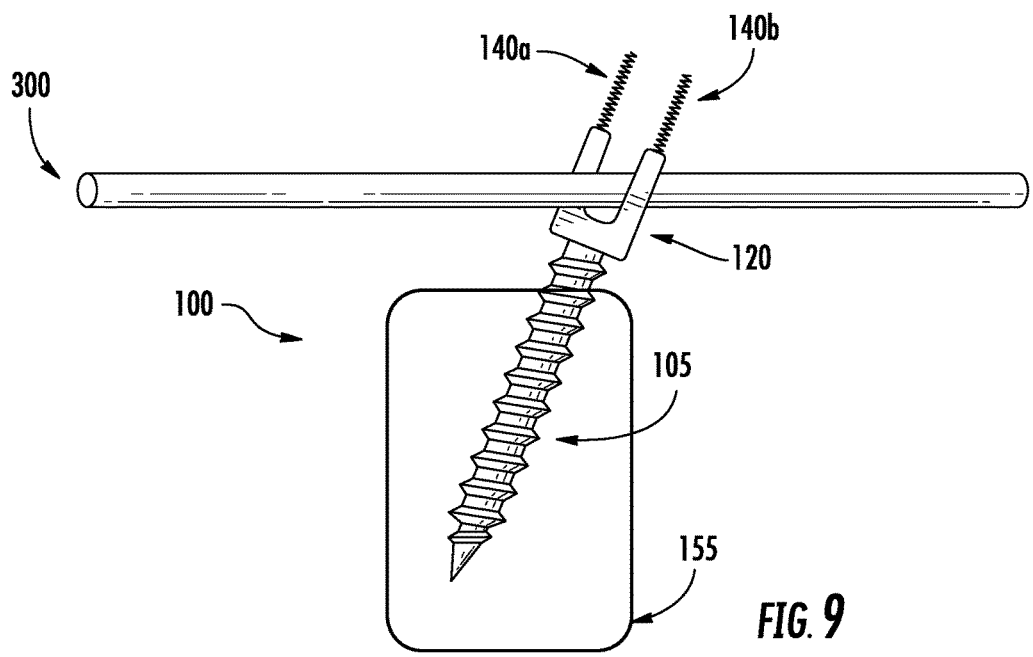
FIG. 9 is a perspective view of a MIS system that includes a pedicle screw or lateral mass screw fixed to a pedicle or lateral vertebral mass and a spinal fixation element situated in the polyaxial screw head of the pedicle screw or lateral mass screw in accordance with the present disclosure.
Figure 10:
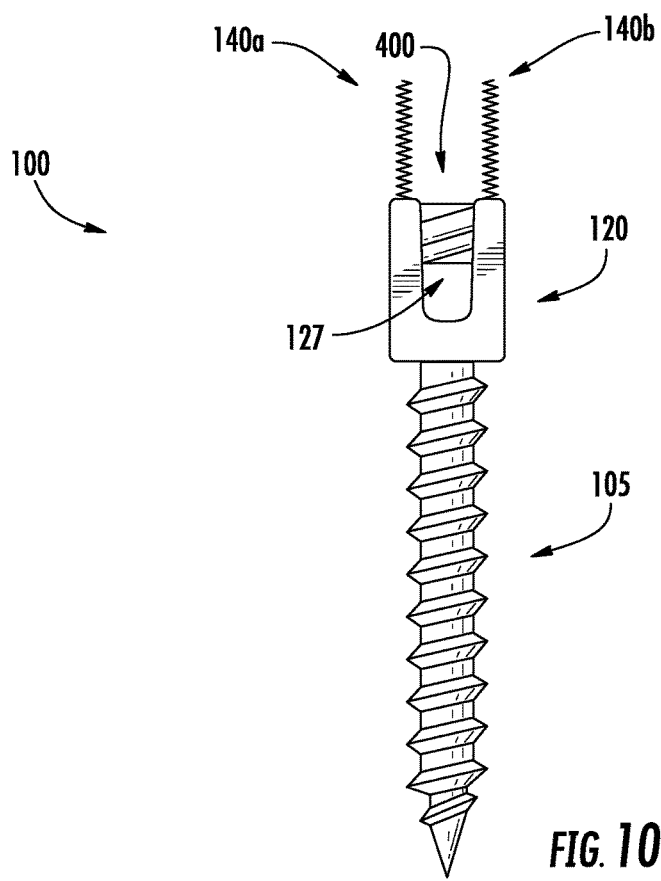
FIG. 10 is a lateral side view of a MIS system that includes a pedicle screw or lateral mass screw and a set screw in accordance with the present disclosure.

In certain embodiments, the hand-held fixation tool 200 further includes a pair of side arms 250a, 250b each having hook end 255a, 255b that are configured to push the spinal fixation element 300 into the polyaxial screw head 120 (see FIGS. 6-7). The pair of side arms 250a, 250b can be located on the hand-held tool 200 at various suitable locations. In one example, the pair of arms 250a, 250b are integrally formed or operatively coupled to the pivot axis 265 (see FIGS. 6-7). In a second example, a first of the pair of side arms 250a is integrally formed or operatively coupled to either the first manual gripping end 210 or the second distal receiving shaft 245, and a second of the pair of side arms 250b is integrally formed or operatively coupled to either the second manual gripping end 240 or the first distal receiving shaft 215 (not shown).

As shown in FIGS. 2, 4-5, 7 and 10, in certain embodiments, the MIS system includes a set screw 400 which is configured to lock the spinal fixation element 300 to the polyaxial screw head 120 (see FIGS. 3-9 for spinal fixation element 300). In certain embodiments, the hand-held fixation tool 200 further includes a screw driver 500 located between the first scissor arm 205 and the second scissor arm 235 to secure the set screw 400 to the polyaxial screw head 120 above the spinal fixation element 300 (see FIGS. 4-5 and 7).

Also provided herein are methods for securing a pedicle screw or lateral mass screw 100 to a vertebral lateral mass or pedicle 155 and for securing a spinal fixation element 300 and a set screw 400 to the pedicle screw or lateral mass screw 100 for vertebrae stabilization. It will be understood by those of ordinary skill in the art that additional or fewer steps may be performed in certain embodiments. In one example, the method includes providing one or more pedicle screws or lateral mass screws 100, like the ones described above, each comprising, for example, a screw shaft 105, a polyaxial screw head 120, and two or more semi-rigid, non-wire, elongated projections 140a, 140b extending from the polyaxial screw head 120, and then implanting the pedicle screw or lateral mass screw 100 in a spine by screwing the pedicle screw or lateral mass screw 100 into a pedicle or lateral vertebral mass 155 (see FIGS. 1, 8-9 for example).

The method can further include providing a hand-held fixation tool 200, like the one described above, comprising, for example, a first scissor arm 205 and a second scissor arm 235 (see FIGS. 3-7 for example).

The method can further include securing a spinal fixation element 300 to the polyaxial screw head 120. This can be performed by, for example, inserting a first semi-rigid, non-wire, elongated projection 140a into the first bore 220 of the first distal receiving shaft 215 of the first scissor arm 205, inserting the second semi-rigid, non-wire, elongated projection 140b into the second bore 260 of the second distal receiving shaft 214 of the second scissor arm 235, and then pushing the spinal fixation element 300 into the polyaxial screw head 120 using the hand-held fixation tool 200 (see FIGS. 6-7 for example).

The method can further include, after securing the spinal stabilization rod 300 to the polyaxial screw head 120, securing a set screw 400 to the polyaxial screw head 120 above the spinal stabilization rod 300 using the hand-held fixation tool 200. The hand-held fixation tool 200 further includes, in certain embodiments, a screw driver 500 located between the first scissor arm 205 and the second scissor arm 235 that assists in securing the set screw 400 to the polyaxial screw head 120 (see FIGS. 3-7 for example). The method can further include, after the set screw 400 has been secured to the polyaxial screw head 120, cutting at least one of the two non-wire guiding elements 140a, 140b from the polyaxial screw head 120.

The systems and methods described above provide substantial benefits over the prior art. As indicated previously, some prior art systems rely on the use of flexible wires for guiding rods to screw heads, but those systems are prone to problems as the flexible wires readily become tangled as flexible wires cannot withstand the force of soft tissue pushing against them. Moreover, some prior art systems employ a non-circular rigid shaft, which is also not optimal as a surgeon would not be able to change the angle of the rigid shaft during the rod insertion process.

In accordance with the present disclosure, the use of two or more semi-rigid, non-wire elongated projections 140a, 140b provides a semi rigid path to the screw head, which alleviates certain issues found in the use of flexible wires or non-circular rigid shafts. For example, the two or more semi-rigid, non-wire elongated projections 140a, 140b are flexible enough to be selectively moved by a doctor during surgery, yet are not prone to substantial entanglement as compared to flexible wires.

The MIS system and several of the various components described above, such as the polyaxial screw head 120, the threaded shaft 105, the spinal fixation element 300, and the set screw 400, can be created from various types of suitable materials such as, for example, biocompatible materials like titanium and polyethylene ketone. Certain parts can be created through 3D printing and/or through other suitable processes as known to those having ordinary skill in the art.

A number of embodiments of the invention have been described. Nevertheless, it will be understood that various modifications may be made without departing from the spirit and scope of the invention. Accordingly, other embodiments are within the scope of the following claims.

Disclosed are materials, systems, devices, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed, that while specific reference of each various individual and collective combinations and permutations of these components may not be explicitly disclosed, each is specifically contemplated and described herein. For example, if a method is disclosed and discussed, each and every combination and permutation of the method and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods and that each such combination or subset of combinations is specifically contemplated and should be considered disclosed.

Publications cited herein and the materials for which they are cited are hereby specifically incorporated by reference in their entireties.

What is claimed is:

1. A method comprising:
   providing a pedicle screw or lateral mass screw comprising:
      a screw shaft comprising an elongated threaded body having a vertical axis;
      a polyaxial screw head comprising two opposite walls that define a concave channel, wherein each of the two opposite sidewalls include a respective top surface that defines a horizontal plane, wherein the horizontal plane is perpendicular to the vertical axis; and
      two semi-rigid elongated projections extending from the two opposite walls at a positive angle in relation to the horizontal plane, wherein at least a portion of each of the two semi-rigid elongated projections is above the horizontal plane, and wherein the two semi-rigid elongated projections are configured to have a height that is at or above a level of a skin incision after implantation of the pedicle screw or lateral mass screw in a pedicle or lateral mass;
   providing a hand-held fixation tool comprising:
      a first scissor arm having a first manual gripping end and a first distal receiving shaft comprising a first bore, wherein a first of the two semi-rigid elongated projections of the polyaxial screw is sized to fit within the first distal receiving shaft; and
      a second scissor arm having a second manual gripping end and a second distal receiving shaft comprising a second bore, wherein a second of the two semi-rigid elongated projections of the polyaxial screw is sized to fit within the second distal receiving shaft, wherein the first and second scissor arms are pivotably coupled about a pivot axis;
   implanting the pedicle screw or lateral mass screw in a spine by screwing the pedicle screw or lateral mass screw into a pedicle or lateral vertebral mass; and
   securing a spinal fixation element to the polyaxial screw head by at least:
      inserting the first semi-rigid elongated projection into the first bore of first distal receiving shaft of the first scissor arm;
      inserting the second semi-rigid elongated projection into the second bore of the second distal receiving shaft of the second scissor arm; and
      pushing the spinal fixation element into the polyaxial screw head using the hand-held fixation tool.

2. The method of claim 1, wherein the spinal fixation element is a spinal stabilization rod.

3. The method of claim 2 further comprising after securing the spinal stabilization rod to the polyaxial screw head, securing a set screw to the polyaxial screw head above the spinal stabilization rod using the hand-held fixation tool, wherein the hand-held fixation tool further includes a screw driver located between the first scissor arm and the second scissor arm.

4. The method of claim 3 further comprising cutting at least one of the two semi-rigid elongated projections from the polyaxial screw head after the set screw has been secured to the polyaxial screw head.

5. The method of claim 1, wherein the angle is selected from a range of angles comprising 5 degrees to, and including, 90 degrees.

6. The method of claim 1, wherein each of the two semi-rigid elongated projections has a diameter of 1 millimeter or greater.

* * * * *